United States Patent
Masaki

[11] Patent Number: 5,133,351
[45] Date of Patent: Jul. 28, 1992

[54] LOW-FREQUENCY ELECTROTHERAPEUTIC DEVICE

[75] Inventor: Kazumi Masaki, Osaka, Japan
[73] Assignee: Ken Hayashibara, Okayama, Japan
[21] Appl. No.: 492,230
[22] Filed: Mar. 14, 1990

Related U.S. Application Data

[63] Continuation of Ser. No. 233,547, Aug. 18, 1988, abandoned.

[30] Foreign Application Priority Data

Aug. 27, 1987 [JP] Japan ............... 62-213653

[51] Int. Cl.$^5$ .................................. A61N 1/00
[52] U.S. Cl. .................. 128/419 R; 128/421; 128/422
[58] Field of Search ............. 128/419 R, 421, 422; 604/20

[56] References Cited

U.S. PATENT DOCUMENTS

| | | | |
|---|---|---|---|
| 3,983,881 | 10/1976 | Wickham | 128/421 |
| 4,164,226 | 8/1979 | Tapper | 128/419 R |
| 4,211,222 | 7/1980 | Tapper | 604/20 |
| 4,301,794 | 11/1981 | Tapper | 128/419 R |
| 4,340,047 | 7/1982 | Tapper et al. | 604/20 |

FOREIGN PATENT DOCUMENTS

| | | |
|---|---|---|
| 0138347 | 4/1985 | European Pat. Off. |
| 0154976 | 9/1985 | European Pat. Off. |
| 1175372 | 3/1962 | Fed. Rep. of Germany |
| 364722 | 11/1981 | Fed. Rep. of Germany |
| 2215199 | 8/1974 | France |
| 2540729 | 8/1984 | France |
| 2584932 | 1/1987 | France |

Primary Examiner—Edgar S. Burr
Assistant Examiner—Aaron J. Lewis
Attorney, Agent, or Firm—Browdy and Neimark

[57] ABSTRACT

A novel low-frequency electrotherapeutic device wherein a low-frequency voltage having a ratio of positive voltage component to negative voltage component in the range of about 0.1:1–0.5:1 is used. The electrotherapeutic device can be advantageously used to massage human body or to iontophorese medicament thereinto without causing unwanted discomforts such as pain, inflammation and burning which are inevitable in conventional low-frequency electrotherapy.

4 Claims, 5 Drawing Sheets

LOW-FREQUENCY ELECTROTHERAPEUTIC DEVICE

This application is a continuation of application Ser. No. 07/223,547, filed Aug. 18, 1988 now abandoned.

BACKGROUND OF THE INVENTION

1. Field of the Invention

The present invention relates to a low-frequency electrotherapeutic device, specifically, to that wherein its low-frequency voltage has a ratio of positive voltage component to negative voltage component in the range of about 0.1:1–0.5:1.

2. Description of the Prior Art

In a massotherapy wherein a low-frequency voltage is applied to human body, it is recommendable to use a low-frequency voltage with a sharp waveform consisting of a rapid rise and a slow fall. Low-frequency voltages with a logarithmic or square waveform have been frequently used in the past because they fulfill these requirements.

The low-frequency voltages may achieve a satisfactory efficacy when their duration conforms to the chronaxy of the muscle being treated, but frequently lead to a painful unsatisfactory treatment because the chronaxy greatly varies with individual sites in a human body.

SUMMARY OF THE INVENTION

With the viewpoint that a ratio of positive voltage component to negative component is an important factor for low-frequency treatment voltage, the present inventor investigated various means wherein these drawbacks of conventional low-frequency electrotherapeutic device are greatly reduced or even eliminated.

As the result, the present inventor found that an extremely efficacious massotherapy can be attained without causing unwanted pain when the ratio is in the range of about 0.1:1–0.5:1.

More particularly, the present invention relates to a low-frequency electrotherapeutic device to apply a low-frequency voltage to a human body, characterized in that said low-frequency voltage has a ratio of positive voltage component to negative voltage component in the range of about 0.1:1–0.5:1.

BRIEF DESCRIPTION OF THE DRAWINGS

The present invention will hereinafter be explained in detail with reference to the accompanying drawings, in which.

DETAILED DESCRIPTION OF THE PREFERRED EMBODIMENTS

Figure 1:
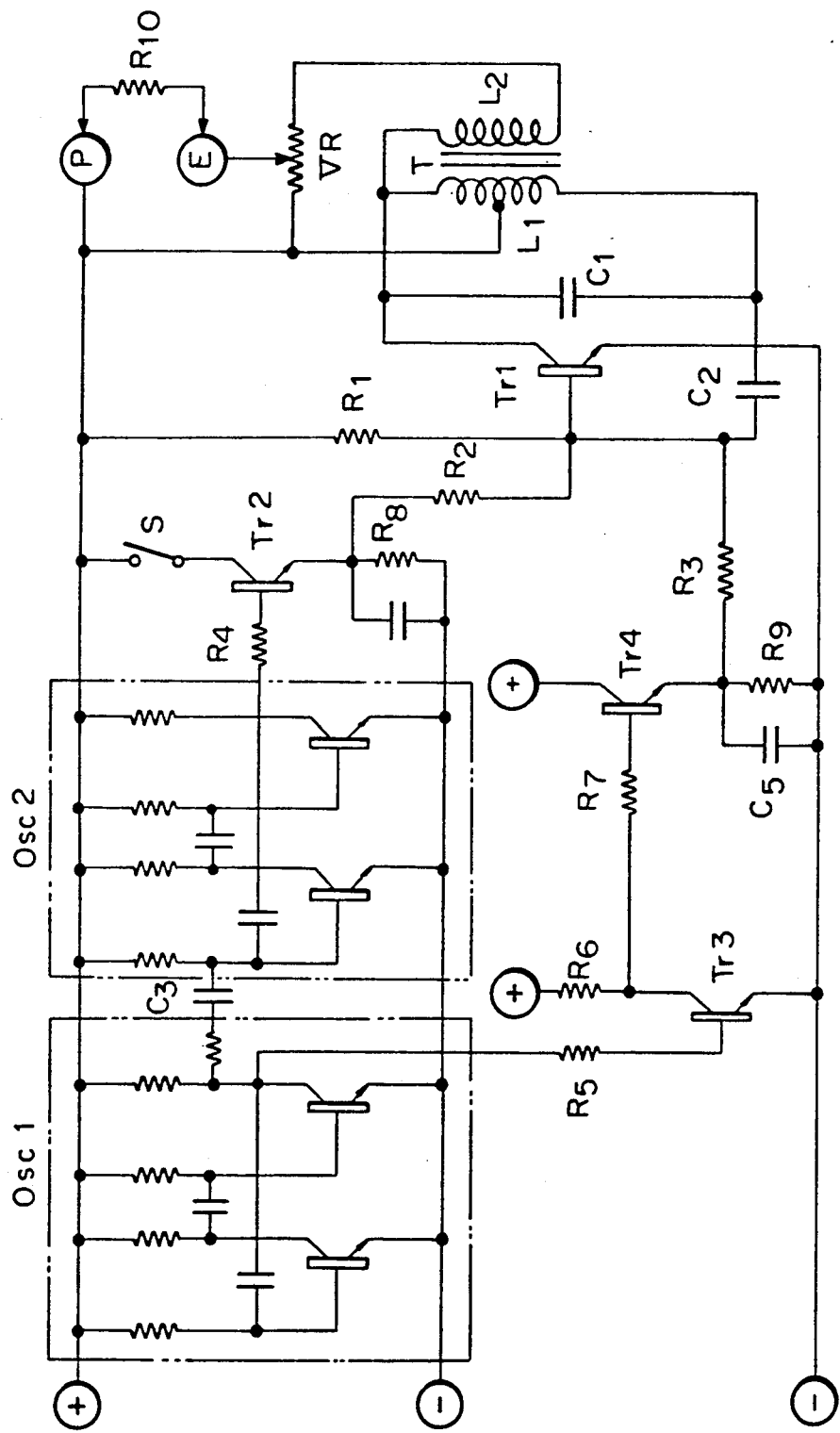
FIG. 1 is the circuit of an embodiment according to the invention.

Throughout the drawings, symbols $R_1$–$R_{10}$ designate resistors; $C_1$–$C_6$, capacitors; $Tr_1$–$Tr_4$, transistors; T, transformer; $L_1$ and $L_2$, windings; VR, variable resistor; $Osc_1$ and $Osc_2$, multivibrators; S, switch; reference numeral 1, cover member; 2, sponge member; 3, metal plate; 4, pressure-sensitive resistor; 5, insulating material; 6, guide; 7, lead; 8, basal plate; 9, fulcrum; 10, leaf spring member; 11, 2P plug: and 12, 2P socket.

Figure 2:
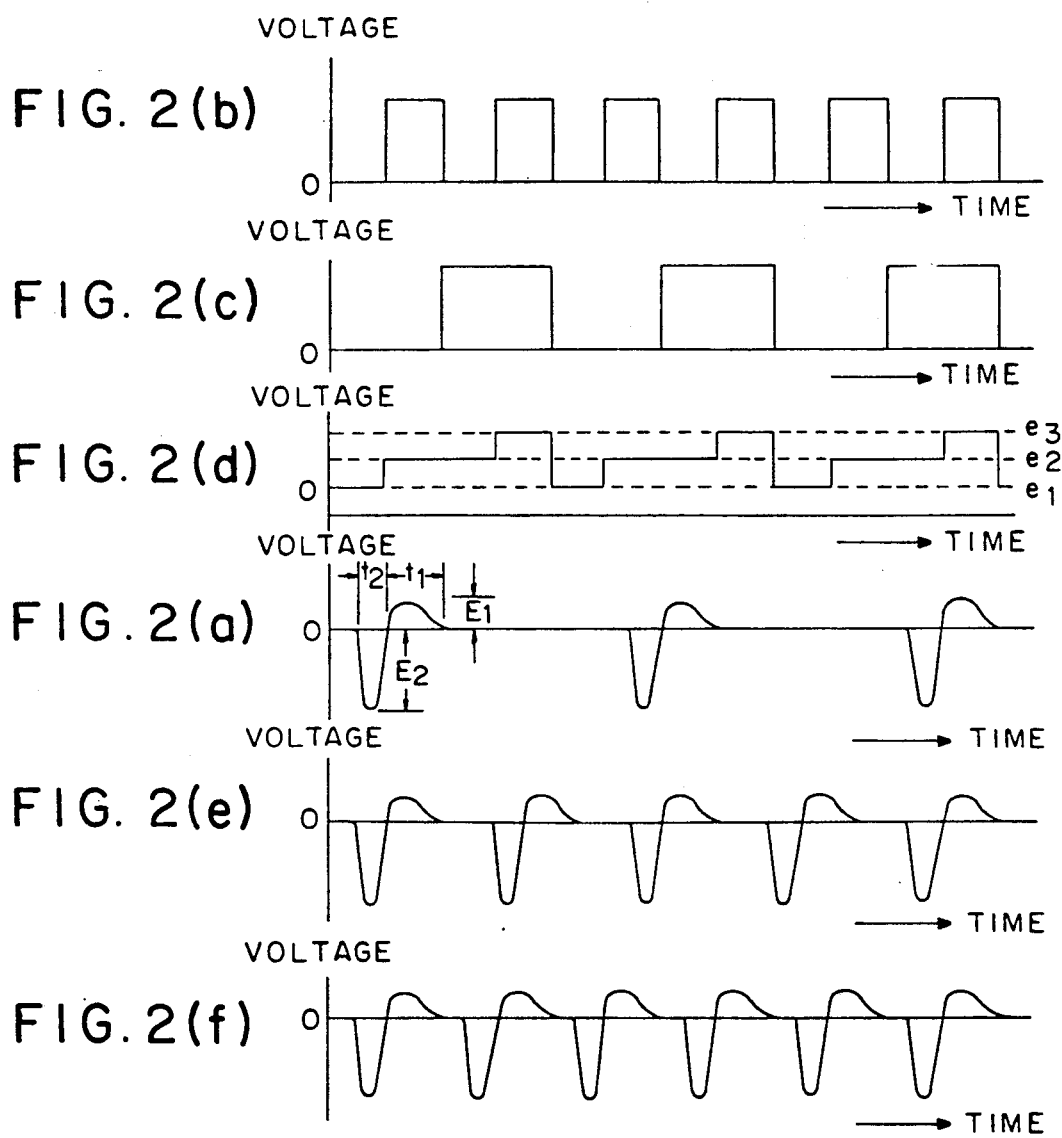
FIGS. 2a–2f are the waveforms appearing in the circuit.

In the circuit as shown in FIG. 1, a blocking oscillator comprising transistor $Tr_1$ and transformer T is to generate a pulsating voltage that has a diphasic action potential waveform with a ratio of positive component $E_1$ to negative component $E_2$ in the range of about 0.1:1–0.5:1, as shown in FIG. 2(a).

The diphasic action potential, a pulsating voltage found in a stimulated nerve, consists of a pair of positive voltage and negative voltage components both having a sharp spike. The aforementioned blocking oscillator is to generate by electronic circuitry the diphasic action potential that is usually found only in a stimulated nerve.

In the blocking oscillator, capacitors $C_1$ and $C_2$ connected with primary winding $L_1$ of transformer T, resistors $R_1$, $R_2$ and $R_3$, and variable resistor VR are to control the ratio of positive voltage component $E_1$ to negative voltage component $E_2$ in the diphasic action potential, as well as to control its pulse interval. A low-frequency voltage that is advantageously usable in massotherapy can be obtained by controlling the values of the capacitors and resistors to give a ratio of positive voltage component $E_1$ to negative voltage component $E_2$ in the range of about 0.1:1–0.5:1, preferably, about 0.2:1–0.3:1. In the same way, pulse duration $t_2$ of negative voltage component $E_2$ in one pulsating wave is set in the range of about 0.001–0.01 second, preferably, about 0.002–0.005 seconds, while duration $t_1$ of positive voltage component $E_1$ is brought to from 1.1- to 2.0-folds, preferably, from about 1.4- to 1.6-folds of duration $t_2$.

The present inventor tested various pulsating voltages including diphasic action potential-, square- and logarithmic-waves on their ratio of positive voltage component to negative voltage component, as well as on their massaging and side effects. The test revealed that a ratio lower than about 0.1:1 or higher than about 0.5:1 did not attain a desired massaging effect instead unwanted side effects such as pain and drying of the skin arose.

In this embodiment, the pulse interval of a treatment voltage across electrodes P and E can be increased and decreased at prescribed time intervals by taking advantage of an intrinsic property a blocking oscillator, so that the response to the treatment voltage in the affected site never decreases or weakens to an undesirable level. The intrinsic property is that the pulse interval in an output from the blocking oscillator greatly varies with the base voltage of transistor $Tr_1$: A relatively high base voltage leads to a shortened pulse interval, while a relatively low base voltage leads to an elongated pulse interval.

More particularly, an output terminal of multivibrator $Osc_1$ generating a square wave with a relatively short period as shown in FIG. 2(b) is connected with an input terminal of multivibrator $Osc_2$ that generates a square wave with a relatively long period as shown in FIG. 2(c). An output terminal of multivibrator $Osc_2$ is connected with an input terminal of an emitter follower comprising transistor $Tr_2$ and exhibiting a time constant. An output terminal of the emitter follower is connected with the base of transistor $Tr_1$ in the aforementioned blocking oscillator through resistor $R_2$. An output of multivibrator $Osc_1$ is supplied to the base of transistor $Tr_1$ in the blocking oscillator through resistor $R_3$ and an emitter follower comprising shaper transistor $Tr_3$ and transistor $Tr_4$ and exhibiting a time constant.

By this arrangement, when both multivibrators $Osc_1$ and $Osc_2$ are out of operation, voltage $e_1$ shown in FIG. 2(d) is applied to the base of transistor $Tr_1$ from a power source; when only multivibrator $Osc_1$ is in operation, voltage $e_2$, which is higher than voltage $e_1$, is applied to the base; when both multivibrators $Osc_1$ and $Osc_2$ are in operation, much higher voltage $e_3$ is applied to the base. When the voltage across the base stepwise elevates in this manner, the pulse interval of an output from the blocking oscillator stepwise shortens as shown in FIGS. 2(a), 2(e) and 2(f) in the given order.

The pulse interval is usually set to 1-200 hertz in terms of its period. Generally, pulse interval closely relates to the refractory period in electrotherapy. Thus, the frequency that is stimulative to human body is dependent on the refractory period, and the upper limit of such frequency is usually found in the range of 400-2,000 hertz. It was confirmed that a pulsating voltage having a pulse interval in the above range exerts the possible highest efficacy when used in this embodiment.

Since in this embodiment switch S is inserted in a collector circuit including transistor $Tr_2$, the pulse interval of the blocking oscillator can be stepwise or non-stepwise increased and decreased at prescribed time intervals by controlling the operation of transistor $Tr_2$ with switch S.

In case that the pulse interval of the blocking oscillator is non-stepwise increased and decreased at prescribed time intervals, switch S, multivibrator $Osc_1$, and the emitter follower comprising shaper transistor $Tr_3$ and transistor $Tr_4$ in FIG. 1 may be omitted to simplify the overall arrangement of the embodiment.

By applying a human body a pulsating voltage that increases and decreases through two or three steps at appropriate time intervals, for example, of 0.5-5 seconds, preferably, 1-2 seconds, a much more comfortable massotherapy is achievable with causing much less pain than in the case of applying a low-frequency voltage wherein a pulsating voltage as shown in FIG. 2(a), 2(e) or 2(f) repeatedly appears at the same time intervals. Such massotherapy is more effective in promoting the metabolism of the skin.

Conventional electrodes can be used as electrodes P and E. If an inadequately controlled treatment voltage is applied to the patient's body, the patient may experience the discomfort in the form of an electric shock when active electrode P is brought into contact with the patient's skin. Because of this reason, it is recommendable to choose electrodes free of such disadvantage.

Figure 3:
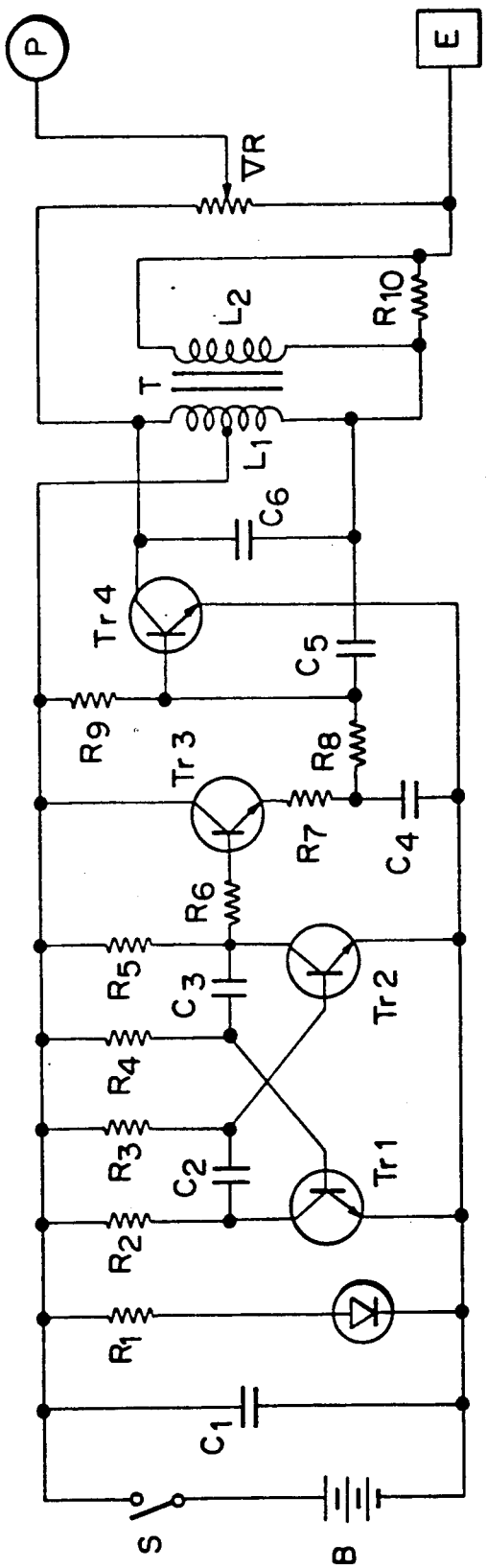
FIG. 3 is the circuit of another embodiment according to the invention.

FIG. 3 is the circuit of another embodiment according to the invention.

In the circuit, a blocking oscillator comprising transistor $Tr_4$ and transformer T is to generate a pulsating voltage that has a diphasic action potential waveform with a ratio of positive voltage component $E_1$ to negative voltage component $E_2$ in the range of about 0.1:1-0.5:1, as shown in FIG. 2(a).

More particularly, both capacitor $C_6$ connected with primary winding $L_1$ of transformer T in the blocking oscillator, and resistor $R_{10}$ connected with secondary winding $L_2$ of transformer T are provided to control the pulse width of the pulsating voltage, as well as to control its ratio of positive voltage component $E_1$ to negative voltage component $E_2$. By changing the values of the resistor and capacitor to control the Q value of a resonant circuit including transformer T, the ratio can be set to about 0.1:1-0.5:1, preferably, about 0.2:1-0.3:1. In the same way, pulse duration $t_2$ of negative voltage component $E_2$ in one pulsating wave can be set to about 0.001-0.01 second, preferably, about 0.002-0.005 seconds, while duration $t_1$ of positive voltage component $E_1$ is set to from about 1.1- to about 2.0-folds, preferably, from about 1.4- to about 1.6-folds of duration $t_2$. The treatment voltage thus obtained is advantageously usable in massotherapy.

In this embodiment, an output terminal of a multivibrator which comprises transistors $Tr_1$ and $Tr_2$ and generates a square wave as shown in FIG. 2(c) is connected with an input terminal of an emitter follower that comprises transistor $Tr_3$ and exhibits a time constant. An output terminal of the emitter follower is connected with the base of transistor $Tr_4$ in the aforementioned blocking oscillator. By supplying the square wave to the blocking oscillator through the emitter follower to bias the base of transistor $Tr_4$, a train of pulsating voltage having a diphasic action potential waveform is intermittently energized across electrodes P and E.

In this case, the pulse interval in one train is appropriately set in the range having an upper limit, usually, of 400-2,000 hertz, similarly as in the preceding embodiment.

In this embodiment, the ratio of positive voltage component to negative voltage component in a treatment voltage is controlled by changing the Q value of the resonant circuit including transformer T. A desired voltage ratio can be easily attained, for example, by connecting a diode and a resistor, preferably, a series circuit of a diode and a variable resistor, between electrodes P and E in a forward direction with respect to the power source being connected, and changing the value of the variable resistor to increase or decrease the positive voltage component.

The present low-frequency electrotherapeutic device can be used to iontophorese medicaments, as well as to conduct massotherapy.

More particularly, since the low-frequency electrotherapeutic device of the invention generates a low-frequency voltage having a ratio of positive voltage component to negative voltage component in the range of about 0.1:1-0.5:1, in other words, a low-frequency voltage having negative voltage component larger in magnitude than positive voltage component, the device can be advantageously used to iontophorese medicaments which negatively charge in solution, such as acetic acid, kojic acid and vitamin C. Such iontophoresis is very effective in treating or removing dermatophytosis and deposited pigments. In this case, superposition of the aforementioned low-frequency voltage, in particular, that having a diphasic action potential waveform, on a square wave voltage without positive voltage component, frequency of about 0.1-10 hertz, preferably, about 0.5-5 hertz, enables a more efficient iontophoresis of the medicaments.

Furthermore, since a low-frequency voltage having a ratio of positive voltage component to negative voltage component in the range of about 0.1:1-0.5:1 scarcely causes discomfort, pain, inflammation or burns when applied to the skin, it comfortably and efficiently iontophoreses medicaments which positively charge in solution, for example, aminovinyl photosensitizing dyes when such low-frequency voltage, preferably, that having a diphasic action potential waveform, frequency, for example, of about 0.1-10 hertz, preferably, about 0.5-5 hertz, is superposed on a square wave voltage without negative voltage component.

In either case, one can employ an arrangement wherein a square wave having a frequency of about 0.1-10 hertz, preferably, about 0.5-5 hertz, is used as the power source, for example, for a blocking oscillator generating a low-frequency voltage with a diphasic action potential waveform, while another square wave that is different in phase from the former square wave, frequency, for example, of about 0.1-10 hertz, preferably, about 0.5-5 hertz, is applied across electrodes P and E in such manner that the low-frequency voltage and a dc voltage without positive or negative voltage component are successively applied to the electrodes at the period of the square wave; or that a low-frequency voltage having a diphasic action potential waveform with a slightly long pulse interval is superposed on the dc voltage. By either arrangement, a massaging effect of the present device and a pharmaceutically effective component iontophoresed in the deeper part of the skin synergistically cooperate to give an extremely high efficacy.

Figure 4:
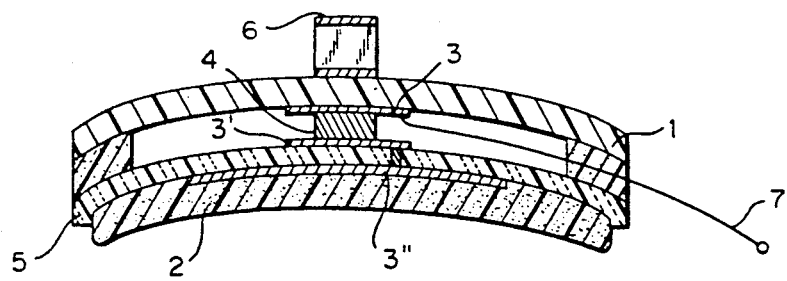
FIG. 4 is the vertical side elevation view of an electrode using a pressure-sensitive resistor.
Figure 5:
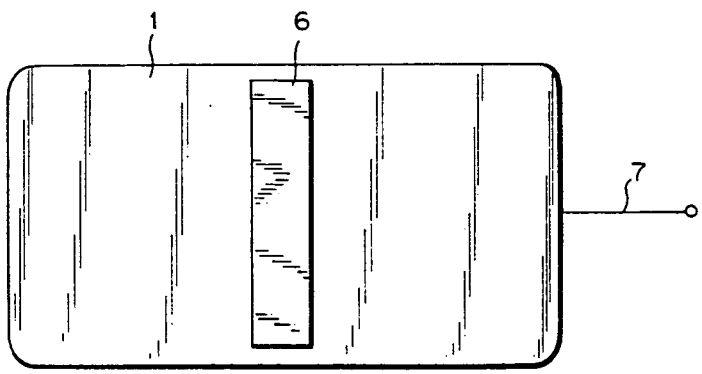
FIG. 5 is the plane view of the electrode.
Figure 6:
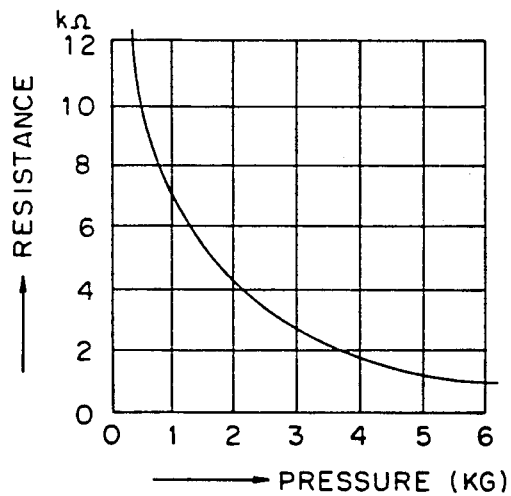
FIG. 6 graphically shows the relationship between the pressure to a pressure-sensitive resistor and its electric resistance.

FIGS. 4 and 5 are illustrative of an electrode which serves as a variable resistor as well, wherein metal plate (3), pressure-sensitive resistor (4), metal plate (3'), insulating member (5) and metal plate (3") are prepared into one body by laminating them in layers between sponge member (2) and curved plastic cover member (1) bearing guide (6) so that the user can handle the electrode. Metal plates (3') and (3") are electrically connected each other, and lead (7) is connected to metal plate (3). Pressure-sensitive resistor (4) has the feature that its electric resistance is relatively high at ambient pressure but decreases as shown in FIG. 6 when pressured.

In use, the user connects the electrode with an output terminal of the circuit shown in FIG. 1 or 3, inserts the hand in guide (6), and places on the skin sponge member (2) which has been soaked in water or an aqueous electrolyte solution. In this case, the magnitude of a treatment voltage across the skin can be finely controlled by increasing or decreasing the pressure to the electrode while allowing sponge member (2) to contact with the skin.

Figure 7:
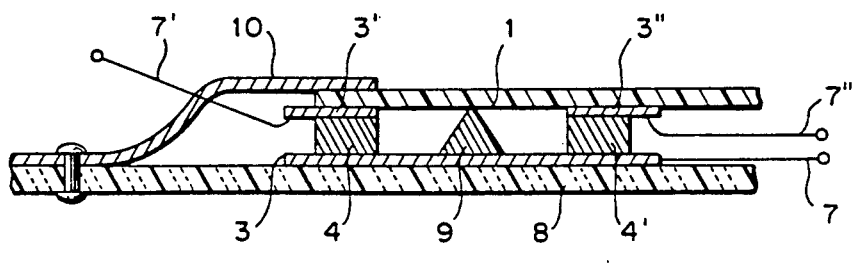
FIG. 7 is the vertical side elevation view of a variable resistor using a pressure-sensitive resistor.

FIG. 7 is illustrative of a variable resistor using a pressure-sensitive resistor, which is advantageously usable as variable resistor VR in the circuit shown in FIG. 1 or 3.

In this variable resistor, metal plate (3) bearing lead (7) is attached to insulating basal plate (8), while pressure-sensitive resistors (4)(4') are attached to metal plate (3) through (9) to leave an appropriate spacing. Insulating cover member (1) is placed over pressure-sensitive resistors (4)(4') through metal plates (3')(3") having lead (7')(7") respectively, while one end of cover member (1) is elastically fixed to basal plate (8) with leaf spring (10).

When out of use, pressure-sensitive resistor (4) located at the side pressured by leaf spring member (10) exhibits a relatively low resistance, while pressure-sensitive resistor (4') located at the side without pressure exhibits a relative high resistance. When in use, the magnitude of a treatment voltage across leads (7)(7') or leads (7)(7") can be adequately controlled by increasing or decreasing the pressure to pressure-sensitive resistor (4') through cover member (1) to change the electric resistance of pressure-sensitive resistors (4)(4') with respect to fulcrum (9).

Figure 8:
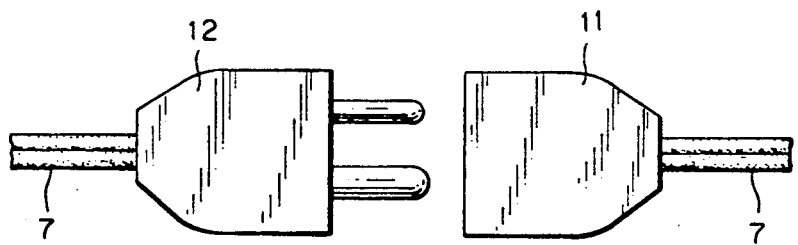
FIG. 8 is the plane view of a plug/socket combination for the connection of electrode.

Leads (7)(7') or leads (7)(7") and an output terminal of a low-frequency oscillator can be conveniently interconnected by using a pair of 2P plug (11) and 2P socket (12) as shown in FIG. 8 wherein the size of plugs is changed in accordance with polarity. In this case, by further changing the distance between the plugs in accordance with the magnitude of the voltage to be applied, the user neither applies a high voltage to the site to be applied with a low voltage nor connects a plug to a socket with wrong polarity.

Figure 9:
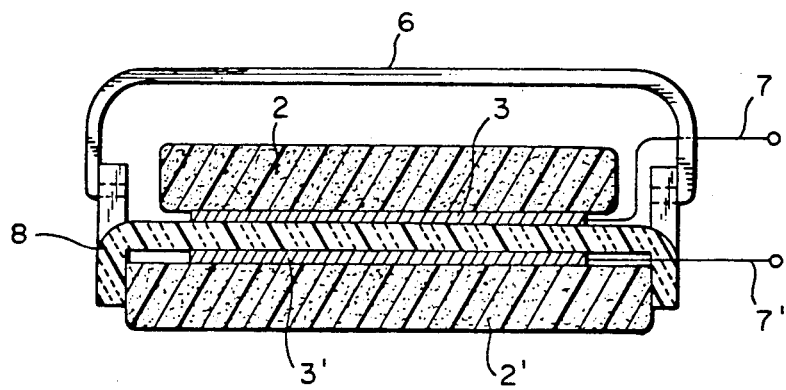
FIGS. 9 and 10 are the vertical side elevation views of an electrode which serves as an active and a dispersive electrodes.

FIG. 9 is illustrative of an electrode arrangement which serves as an active and a dispersive electrodes. Metal plates (3)(3') bearing leads (7)(7') respectively are tightly placed between the upper and lower sides of insulating basal plate (8) which has been attached with guide (6) so that the user can handle the electrode. It is recommendable to prepare the electrode into a curved shape in order to ensure a better fitness to the affected site, similarly as in the case of the electrode shown in FIG. 4.

In use, the electrode is connected with an output terminal of the circuit shown in FIG. 1 or 3, and sponge members (2)(2') are immersed in water or an electrolyte solution, after which the user inserts the hand in guide (6) and places sponge member (2') on the affected site.

The electrode has the features that it enables an efficient therapy of various sites in human body because the user connects only one electrode to a low-frequency electrotherapeutic device and handles the electrode during therapy.

Figure 10:
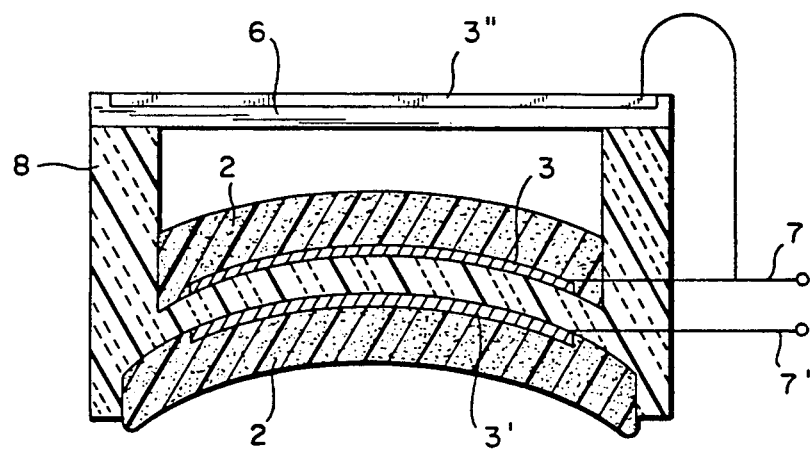

In the electrode a shown in FIG. 10, metal plate (3") is additionally provided on the upper surface of guide (6) in the electrode shown in FIG. 9, and then electrically connected with lead (7).

The electrode has the feature that it reduces electric shock to the hand in contact with the electrode because, when used, for example, in bath, a major part of current flows through an electric resistance that is formed between metal plate (3") and the human body through water.

An active and a dispersive electrode can be connected into one body by attaching a pair of half circular metal plate bearing a lead to a base plate of an insulating material shaped, for example, into triangle, square or circle while electrically insulating the metal plates, and covering the metal plates with a sponge member in the same shape; or concentrically attaching to the basal plate a ring-shaped metal plate having a lead and a ring- or disc-shaped metal plate bearing a lead to leave an appropriate spacing, and covering the metal plates with a sponge member of the same shape.

An active electrode prepared, for example, into a roller shape can be rotatably attached to one end of a vessel containing a low-frequency electrotherapeutic device, while the peripheral part of the vessel to be handled can be covered with a band-shaped dispersive electrode.

Since the present invention is arranged in this way, an extremely efficacious massotherapy can be achieved with causing less pain.

Furthermore, massotherapy using the present electrotherapeutic device helps to promote the metabolism of the scalp. This is effective in promoting the regeneration and growth of hair, as well as in preventing the loss of hair and keeping its health.

In addition, a much higher efficacy is achievable by conducting the massotherapy in bath.

The electrotherapeutic device of the invention has the feature that it enables a comfortable iontophoresis without fear of causing pain, inflammation or burn.

While the prefaced forms of the present invention have been described, it is to be understood that modifications will be apparent to those skilled in the art without departing from the spirit of the invention.

I claim:

1. In a low-frequency electrotherapeutic device which comprises an oscillator capable of generating a low-frequency voltage and a pair of electrodes connected to an output terminal of said oscillator, the low-frequency voltage being applied to a human body through said pair of electrodes, the improvement wherein said low-frequency voltage has a ratio of positive voltage component to negative voltage component in the range of about 0.1:1–0.5:1 and in the low-frequency voltage its reverse energy is larger than forward energy thereof.

2. The device of claim 1, wherein said low-frequency voltage is a pulsating voltage having a pulse interval.

3. The device of claim 2, wherein the pulse interval of said pulsating voltage increases and decreases at prescribed time intervals.

4. The device of claim 1, wherein said low-frequency voltage has a diphasic action potential waveform.

* * * * *